US010806336B2

(12) United States Patent
Kaku

(10) Patent No.: US 10,806,336 B2
(45) Date of Patent: Oct. 20, 2020

(54) ENDOSCOPIC DIAGNOSIS APPARATUS, LESION PORTION SIZE MEASUREMENT METHOD, PROGRAM, AND RECORDING MEDIUM

(71) Applicant: FUJIFILM Corporation, Tokyo (JP)

(72) Inventor: Toshihiko Kaku, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 562 days.

(21) Appl. No.: 15/690,295

(22) Filed: Aug. 30, 2017

(65) Prior Publication Data

US 2017/0360286 A1 Dec. 21, 2017

Related U.S. Application Data

(63) Continuation of application No. PCT/JP2016/053080, filed on Feb. 2, 2016.

(30) Foreign Application Priority Data

Mar. 31, 2015 (JP) .................. 2015-070703

(51) Int. Cl.
*A61B 1/04* (2006.01)
*A61B 1/06* (2006.01)
(Continued)

(52) U.S. Cl.
CPC ........ *A61B 1/0661* (2013.01); *A61B 1/00009* (2013.01); *A61B 1/04* (2013.01);
(Continued)

(58) Field of Classification Search
CPC ....... A61B 1/04; A61B 1/0661; A61B 1/0676; A61B 1/00009; A61B 5/1079
See application file for complete search history.

(56) References Cited

U.S. PATENT DOCUMENTS 9,301,692 B2 4/2016 Kaji et al.
2009/0244260 A1 10/2009 Takahashi et al.
(Continued)

FOREIGN PATENT DOCUMENTS

JP S58-067230 4/1983
JP S59-071736 4/1984
(Continued)

OTHER PUBLICATIONS

"International Search Report (Form PCT/ISA/210) of PCT/JP2016/053080," dated May 10, 2016, with English translation thereof, pp. 1-5.
(Continued)

*Primary Examiner* — Matthew J Kasztejna
(74) *Attorney, Agent, or Firm* — JCIPRNET

(57) ABSTRACT

There are provided an endoscopic diagnosis apparatus, lesion portion size detection method, and a non-transitory computer-readable recording medium that enable easy detection of the size of a lesion portion using an endoscope. This object is achieved by capturing an endoscopic image by emitting light having a regular repetitive pattern onto a subject, detecting, from the endoscopic image, a region in which a repetitive pattern is different from the repetitive pattern of the emitted light, and detecting at least one of a length and area of a lesion portion by using a number of repetitive patterns in the region in which the repetitive pattern is different and a size of a unit of repetition in the repetitive pattern.

4 Claims, 5 Drawing Sheets

(51) Int. Cl.
*A61B 5/107* (2006.01)
*A61B 5/00* (2006.01)
*A61B 1/00* (2006.01)

(52) U.S. Cl.
CPC .......... *A61B 5/0084* (2013.01); *A61B 5/1076* (2013.01); *A61B 5/1079* (2013.01); *A61B 2505/05* (2013.01); *A61B 2576/00* (2013.01)

(56) References Cited

U.S. PATENT DOCUMENTS

| 2010/0272318 | A1 | 10/2010 | Cabiri et al. |
| 2013/0110006 | A1 | 5/2013 | Sharonov et al. |
| 2014/0276097 | A1 | 9/2014 | Sharonov |
| 2014/0350395 | A1 | 11/2014 | Shachaf et al. |

FOREIGN PATENT DOCUMENTS

| JP | S63-148227 | 6/1988 |
| JP | H03-295532 | 12/1991 |
| JP | 2008-245838 | 10/2008 |
| JP | 2009-240621 | 10/2009 |
| JP | 2010-276540 | 12/2010 |
| JP | 2011-183000 | 9/2011 |
| JP | 2013-257166 | 12/2013 |

OTHER PUBLICATIONS

"Written Opinion of the International Searching Authority (Form PCT/ISA/237) of PCT/JP2016/053080," dated May 10, 2016, with English translation thereof, pp. 1-10.
"Search Report of Europe Counterpart Application", dated Apr. 5, 2018, p. 1-p. 8.
"Notification of Reasons for Refusal of Japanese Counterpart Application No. 2015-070703," dated Oct. 24, 2017, with English translation thereof, pp. 1-7.

FIG. 7A
FIG. 7B
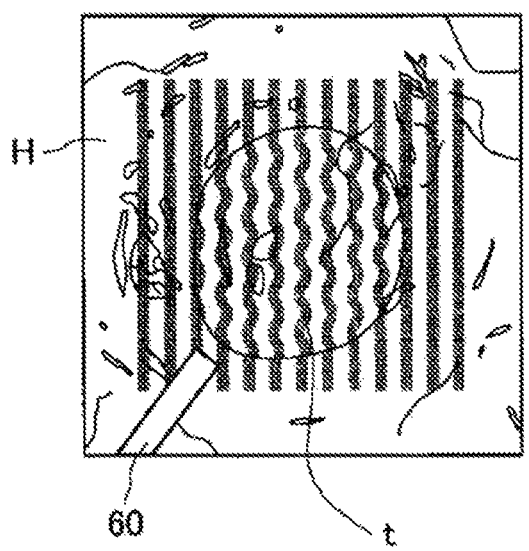
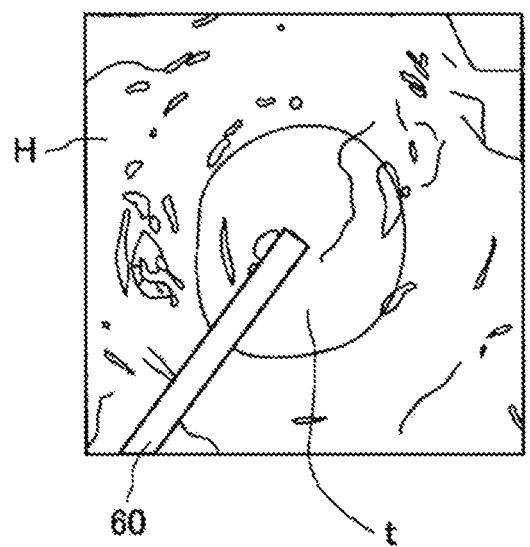

ENDOSCOPIC DIAGNOSIS APPARATUS, LESION PORTION SIZE MEASUREMENT METHOD, PROGRAM, AND RECORDING MEDIUM

CROSS-REFERENCE TO RELATED APPLICATIONS

This application is a Continuation of PCT International Application No. PCT/JP2016/053080 filed on Feb. 2, 2016, which claims priority under 35 U.S.C § 119(a) to Japanese Patent Application No. 2015-070703 filed on Mar. 31, 2015. Each of the above application(s) is hereby expressly incorporated by reference, in its entirety, into the present application.

BACKGROUND OF THE INVENTION

1. Field of the Invention

The present invention relates to size measurement of a lesion portion using an endoscope. Specifically, the present invention relates to an endoscopic diagnosis apparatus, a lesion portion size measurement method that enable easy size measurement of a lesion portion using an endoscope and a non-transitory computer-readable recording medium on which a program relates to size measurement of a lesion portion is recorded.

2. Description of the Related Art

An endoscopic diagnosis apparatus is used to observe the inside of a subject. In the case of observing the inside of a subject, an insertion section of an endoscope is inserted into a body cavity of the subject, white light as observation light, for example, is emitted from a distal end portion of the insertion section onto the subject (a region of interest), reflected light thereof is received, and thereby an endoscopic image is captured. The captured endoscopic image is displayed on a display unit and observed by an operator of the endoscopic diagnosis apparatus.

In recent years, there has been a demand for measuring the size of a lesion portion such as a tumor portion for the purpose of, for example, removing a tumor if the tumor is larger than a predetermined size and conserving the tumor for monitoring if the tumor has the predetermined size or less, as well as determining the presence or absence of a lesion portion by viewing an endoscopic image captured inside a subject.

A method for measuring the size of a lesion portion by using a surgical instrument such as a probe with a scale is known. In this method, a probe with a scale is inserted from a forceps inlet of an endoscope and is protruded from a forceps outlet at a distal end portion of the endoscope. A tip portion of the probe with a scale is flexible and has scales for measuring size. The flexible tip portion is pressed against a subject so as to bend, and the scales on the tip portion are read to measure the size of a lesion portion of the subject.

In this method, however, inserting the probe with a scale into a forceps channel of the endoscope is required only for measuring the size of a lesion portion. This operation is not only time-consuming but also complex and cumbersome. Furthermore, since the measurement is performed by pressing the tip portion of the probe with a scale against a subject so as to bend the tip portion, measurement accuracy is low. In some portions of a subject, it may be difficult to perform measurement, that is, it may be difficult to press the tip portion against the subject.

Various methods for measuring the size of a lesion portion using an endoscope have been proposed.

For example, JP2011-183000A describes ejecting water streams onto a lesion portion from two openings at a distal end portion of an insertion section of an endoscope and determining, on the basis of the distance between the two water streams being equal to the distance between the two openings, whether or not the lesion portion is larger than or equal to a treatment reference value.

In addition, JP2008-245838A describes setting a plurality of measurement points around a lesion portion by using a surgical instrument having an arm portion for setting the measurement points, and obtaining the size of the lesion portion through computation on the basis of coordinate information on the measurement points.

SUMMARY OF THE INVENTION

The endoscopic diagnosis apparatus according to JJP2011-183000A involves an issue that a special endoscope including two openings for ejecting two water streams from the distal end portion of the insertion section is required, and that only this endoscope is capable of measuring the size of a lesion portion.

The endoscopic diagnosis apparatus according to JP2008-245838A involves an issue that a robot arm is required to measure the size of a lesion portion, and that it is necessary to set a plurality of measurement points around the lesion portion by operating the complex robot arm.

An object of the present invention is to solve the issues according to the related art and to provide an endoscopic diagnosis apparatus and a lesion portion size measurement method that enable easy size measurement of a lesion portion such as a tumor portion using an endoscope, and a non-transitory computer-readable recording medium.

To achieve the object, an endoscopic diagnosis apparatus according to the present invention provides an endoscopic diagnosis apparatus including an endoscope having a forceps outlet; light emitting unit for emitting light having a regular repetitive pattern, the light emitting unit being able to be protruded from the forceps outlet; and image analyzing unit for detecting, from an image for measurement which is an image captured by the endoscope in a state where light is emitted by the light emitting unit, a region in which a repetitive pattern is different from the repetitive pattern of the light emitted by the light emitting unit, and calculating at least one of a length and area of a lesion portion by using a number of repetitive patterns in the region in which the repetitive pattern is different and a size of a unit of repetition in the repetitive pattern.

In the endoscopic diagnosis apparatus, it is preferable that the light emitting unit emit parallel light.

Preferably, the light emitting unit emits diffuse light, the endoscopic diagnosis apparatus further includes distance detecting unit for detecting a distance between the light emitting unit and a subject at a time of capturing of the image for measurement, and the image analyzing unit detects the size of the unit of repetition in the repetitive pattern on the subject by using the distance between the light emitting unit and the subject detected by the distance detecting unit and a diffusion angle of the diffuse light.

Preferably, the distance detecting unit detects the distance between the light emitting unit and the subject at the time of capturing of the image for measurement, on the basis of a position of the light emitting unit in the image for measurement and a position of the light emitting unit in an image captured in a state where the light emitting unit is in contact with the subject.

Preferably, the distance detecting unit detects that the light emitting unit has come in contact with the subject, on the basis of a change in an amount of light emitted by the light emitting unit.

Preferably, the regular repetitive pattern of the light emitted by the light emitting unit is a striped pattern or a lattice pattern.

A lesion portion size measurement method according to the present invention provides a lesion portion size detection method including imaging a subject by emitting, with light emitting unit for emitting light having a regular repetitive pattern, the light having the repetitive pattern onto the subject by using an endoscope having a forceps outlet, the light emitting unit being protruded from the forceps outlet; detecting, in an image obtained by imaging the subject, a region in which a repetitive pattern is different from the repetitive pattern of the light emitted onto the subject; and calculating at least one of a length and area of a lesion portion by using a number of repetitive patterns in the region in which the repetitive pattern is different and a size of a unit of repetition in the repetitive pattern.

In the lesion portion size measurement method according to the present invention, it is preferable that the light emitting unit emit parallel light.

Preferably, the light emitting unit emits diffuse light, and the size of the unit of repetition in the repetitive pattern on the subject is detected on the basis of a distance between the light emitting unit and the subject at a time of imaging of the subject through emission of the light having the repetitive pattern, and a diffusion angle of the diffuse light.

Preferably, the distance between the light emitting unit and the subject is detected on the basis of a position of the light emitting unit in the image obtained by imaging the subject by emitting the light having the repetitive pattern and a position of the light emitting unit in an image captured in a state where the light emitting unit is in contact with the subject.

Preferably, the light emitting unit having come in contact with the subject is detected on the basis of a change in an amount of light emitted by the light emitting unit.

Preferably, the repetitive pattern is a striped pattern or a lattice pattern.

A recording medium according to the present invention provides a non-transitory computer-readable recording medium on which a program is recorded, the program causing a computer to execute a step of detecting, from an image obtained by imaging a subject by emitting a regular repetitive pattern, a region in which a repetitive pattern is different from the repetitive pattern of the emitted light; a step of counting a number of repetitive patterns in the region in which the repetitive pattern is different; and a step of calculating at least one of a length and area of a lesion portion by using the number of repetitive patterns in the region in which the repetitive pattern is different and a size of a unit of repetition in the repetitive pattern.

According to the present invention, the size of a lesion portion such as a tumor portion can be easily measured by using an endoscope.

BRIEF DESCRIPTION OF THE DRAWINGS

FIGS. 7A and 7B are conceptual diagrams for describing the lesion portion size measurement method according to the present invention.

DESCRIPTION OF THE PREFERRED EMBODIMENTS

Hereinafter, an endoscopic diagnosis apparatus, lesion portion size measurement method, and a non-transitory computer-readable recording medium according to the present invention will be described in detail on the basis of preferred embodiments illustrated in the attached drawings.

Figure 1:
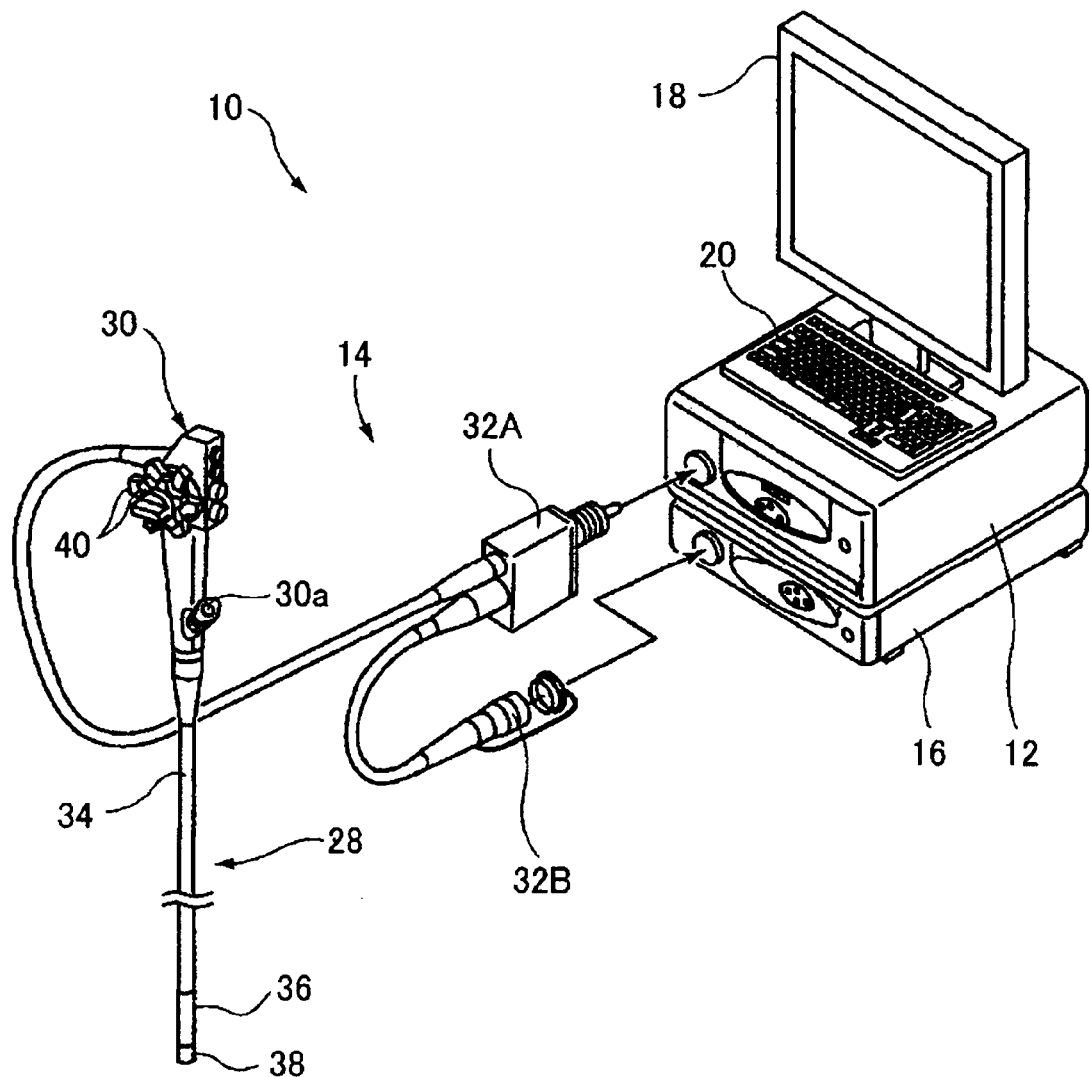
FIG. 1 is a conceptual diagram illustrating an example of an endoscopic diagnosis apparatus according to the present invention.
Figure 2:
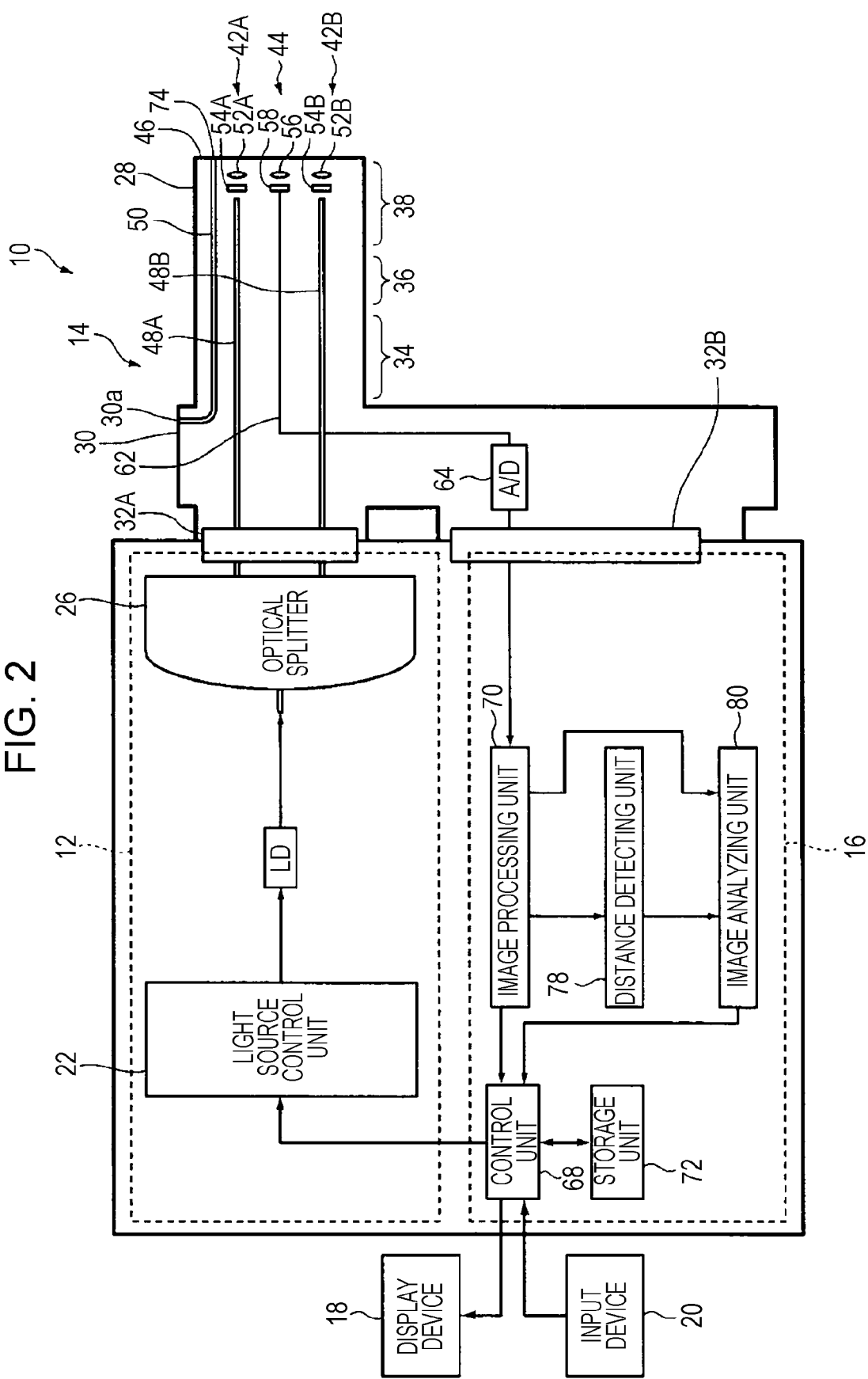
FIG. 2 is a block diagram illustrating the internal configuration of the endoscopic diagnosis apparatus illustrated in FIG. 1.

FIG. 1 conceptually illustrates an example of the endoscopic diagnosis apparatus according to the present invention that executes the lesion portion size measurement method according to the present invention. FIG. 2 is a block diagram illustrating the internal configuration of the endoscopic diagnosis apparatus illustrated in FIG. 1.

As illustrated in FIGS. 1 and 2, the endoscopic diagnosis apparatus 10 is constituted by a light source device 12, an endoscope 14 that captures an endoscopic image of a subject (a region of interest) by using observation light supplied from the light source device 12, a processor device 16 that performs image processing on the endoscopic image captured by the endoscope 14, a display device 18 that displays the endoscopic image that has undergone the image processing and has been output from the processor device 16, and an input device 20 that receives an input operation.

Although not illustrated in FIGS. 1 and 2, the endoscopic diagnosis apparatus 10 has a light emitting probe 60 (an example of light emitting unit) that is inserted from a forceps hole 30a described below, extended through a forceps channel 50, and protruded from a forceps outlet 74, and that emits light having a regular repetitive pattern such as a striped pattern or lattice pattern onto a subject.

As illustrated in FIG. 2, the light source device 12 is constituted by a light source control unit 22, a laser light source LD, and an optical splitter 26.

In the light source device 12 illustrated in the figure, the laser light source LD emits narrowband light having a center wavelength of 445 nm in a predetermined blue wavelength range (for example, the center wavelength±10 nm). The laser light source LD is a light source that emits, as illumination light, excitation light for causing fluorescent bodies described below to generate white light (pseudo white light). ON/OFF (light-up/light-down) control and light amount control of the laser light source LD are performed by the light source control unit 22, which is controlled by a control unit 68 of the processor device 16 described below.

As the laser light source LD, an InGaN-based laser diode of a broad area type can be used. Alternatively, an InGaNAs-based laser diode, a GaNAs-based laser diode, or the like can be used.

A white light source for generating white light is not limited to a combination of excitation light and fluorescent bodies, and any light source that emits white light may be used. For example, a xenon lamp, halogen lamp, white LED (light-emitting diode), or the like can be used. The wavelength of the laser light emitted by the laser light source LD is not limited to the foregoing example, and laser light with a wavelength that plays a similar role can be selected as appropriate.

The laser light emitted by the laser light source LD enters an optical fiber through a condenser lens (not illustrated) and is then transmitted to a connector section 32A after being split into two branches of light by the optical splitter 26. The optical splitter 26 is constituted by a half-mirror, reflection mirror, or the like.

The endoscope 14 is an electronic endoscope having an illumination optical system that emits two branches (two beams) of illumination light from a distal end surface of an insertion section 28 that is to be inserted into a subject, and an imaging optical system of a single system (single lens) type that captures an endoscopic image of a subject.

The endoscope 14 includes the insertion section 28, an operation section 30 that is operated to bend a distal end of the insertion section 28 or to perform observation, the connector section 32A for connecting the endoscope 14 to the light source device 12 in a detachable manner, and a connector section 32B for connecting the endoscope 14 to the processor device 16 in a detachable manner.

On the back surface side of the connector section 32A in FIG. 1, a water supply connector for connecting the endoscope 14 to a water supply source and an air supply connector for connecting the endoscope 14 to an air supply source are disposed.

The endoscope 14 is basically a known electronic endoscope except that the endoscope 14 is applicable to size measurement of a lesion portion described below.

The insertion section 28 is constituted by a flexible portion 34 having flexibility, a bending portion 36, and an endoscope distal end portion 38.

The bending portion 36 is disposed between the flexible portion 34 and the endoscope distal end portion 38 and is configured to be freely bent by a rotational operation of an angle knob 40 located at the operation section 30. The bending portion 36 can be bent in an arbitrary direction or at an arbitrary angle in accordance with a portion or the like of a subject for which the endoscope 14 is used, and accordingly the endoscope distal end portion 38 can be oriented toward a desired portion of interest.

Figure 3:
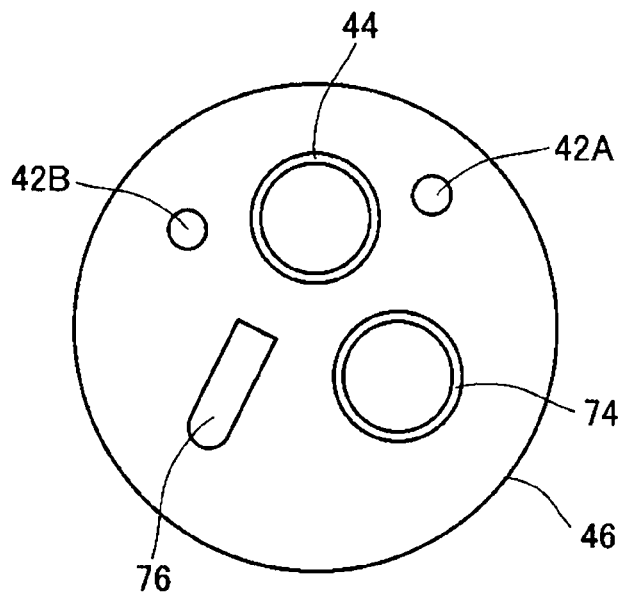
FIG. 3 is a conceptual diagram illustrating the configuration of a distal end portion of an endoscope.

As illustrated in FIG. 3, two illumination windows 42A and 42B for emitting light onto a subject, one observation window 44 for gathering reflected light from the subject, the forceps outlet 74, an air/water supply channel opening 76, and so forth are located on an endoscope distal end surface 46, which is the distal end surface of the insertion section 28 (endoscope distal end portion 38).

The observation window 44, the forceps outlet 74, and the air/water supply channel opening 76 are located in a center portion of the endoscope distal end surface 46. The illumination windows 42A and 42B are located on both sides of the observation window 44 so as to sandwich the observation window 44.

The forceps outlet 74 is an opening serving as an exit for a surgical instrument (probe) such as forceps or the light emitting probe 60 described below. The surgical instrument is inserted from the forceps hole 30a disposed in the operation section 30, extended through the forceps channel 50, and protruded from the forceps outlet 74 on the endoscope distal end surface 46, so as to be used for a medical procedure.

The air/water supply channel opening 76 ejects water and air to wash the observation window 44.

An optical fiber 48A is accommodated behind the illumination window 42A. The optical fiber 48A extends to the light source device 12 through the endoscope distal end portion 38, bending portion 36, and flexible portion 34 of the insertion section 28 and the connector section 32A. A fluorescent body 54A is located in front of a tip portion (on the illumination window 42A side) of the optical fiber 48A, and in addition an optical system such as a lens 52A is attached in front of the fluorescent body 54A. Likewise, an optical fiber 48B is accommodated behind the illumination window 42B. A fluorescent body 54B and an optical system such as a lens 52B are located in front of a tip portion of the optical fiber 48B.

The fluorescent bodies 54A and 54B contain a plurality of kinds of fluorescent substances (for example, a YAG-based fluorescent substance or a fluorescent substance such as BAM ($BaMgAl_{10}O_{17}$)) that absorb a part of blue laser light emitted by the laser light source LD and that are excited to emit light in the green to yellow spectrum. When the fluorescent bodies 54A and 54B are irradiated with excitation light, light in the green to yellow spectrum (fluorescent light) emitted by the fluorescent bodies 54A and 54B as a result of excitation is combined with blue laser light that has passed through the fluorescent bodies 54A and 54B without being absorbed, and thereby white light (pseudo white light) for observation is generated.

Figure 4:
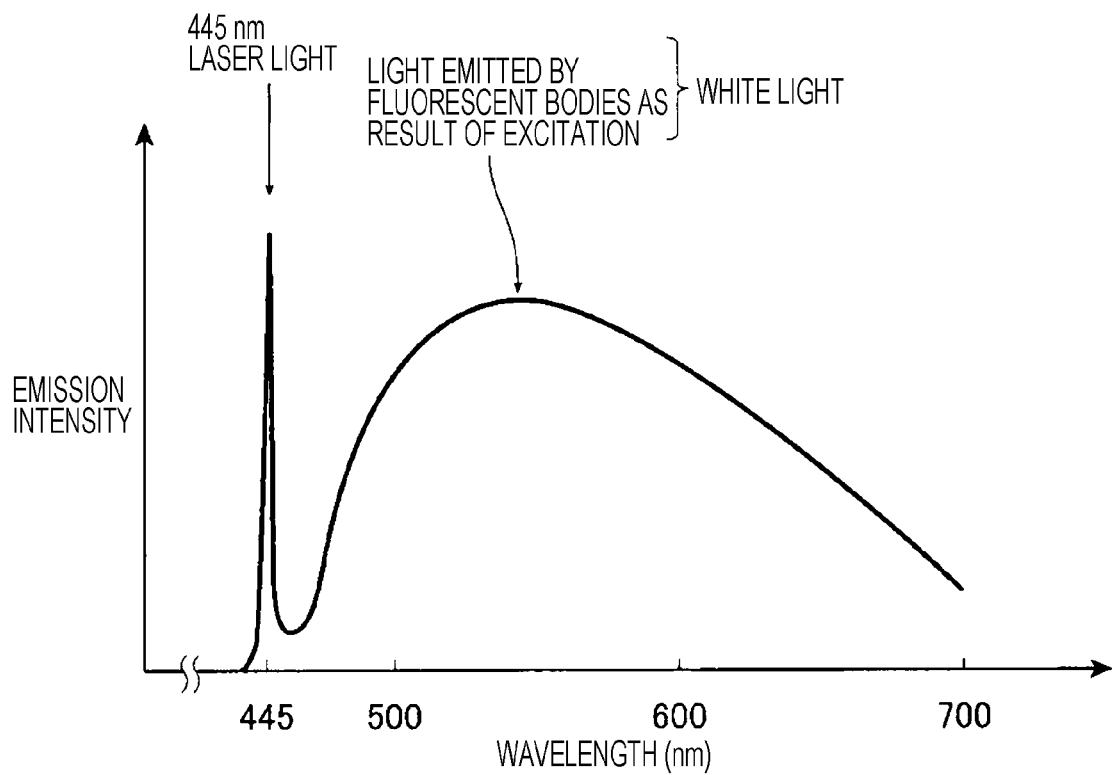
FIG. 4 is a graph illustrating an emission spectrum of blue laser light emitted by a blue laser light source and of light obtained by converting the wavelength of the blue laser light by using fluorescent bodies.

FIG. 4 is a graph illustrating an emission spectrum of blue laser light emitted by the blue laser light source and of light obtained by converting the wavelength of the blue laser light by using fluorescent bodies. The blue laser light emitted by the laser light source LD is expressed by an emission line having a center wavelength of 445 nm, and the light emitted by the fluorescent bodies 54A and 54B as a result of excitation caused by the blue laser light has a spectral intensity distribution in which the emission intensity increases in a wavelength range of about 450 to 700 nm. Composite light of the light emitted as a result of excitation and the blue laser light forms the foregoing pseudo white light.

The white light according to the present invention is not limited to light strictly including all wavelength components of visible light and may be, for example, light including light in specific wavelength bands, for example, wavelength bands of R (red), G (green), and B (blue) as reference colors, as well as the foregoing pseudo white light. That is, the white light according to the present invention includes, in a broad sense, light including green to red wavelength components, light including blue to green wavelength components, and the like.

In the illumination optical system, the configuration and operation of the illumination window 42A side and the illumination window 42B side are equivalent to each other, and basically equivalent illumination light beams are simultaneously emitted from the illumination windows 42A and 42B. Alternatively, different illumination light beams may be emitted from the illumination windows 42A and 42B. It is not required to have an illumination optical system that emits two branches of illumination light. For example, an equivalent function may be implemented by an illumination optical system that emits one or four branches of illumination light.

An optical system, such as an objective lens unit 56, for gathering image light of a subject is attached behind the observation window 44. Furthermore, an imaging device 58, such as a CCD (Charge Coupled Device) image sensor or CMOS (Complementary Metal-Oxide Semiconductor) image sensor, for obtaining image information on the subject is attached behind the objective lens unit 56.

The imaging device 58 receives, at its imaging surface (light receiving surface), light from the objective lens unit 56, photoelectrically converts the received light, and outputs an imaging signal (analog signal). The imaging surface of the imaging device 58 is provided with red (about 580 to 760 nm), green (about 450 to 630 nm), and blue (about 380 to 510 nm) color filters having spectral transmittance for splitting a wavelength range of about 370 to 720 nm of visible light into three bands, and a plurality of sets of pixels, each set formed of pixels of three colors, R pixel, G pixel, and B pixel, are arranged in a matrix on the imaging surface.

The light beams guided by the optical fibers 48A and 48B from the light source device 12 are emitted from the endoscope distal end portion 38 toward a subject. Subsequently, an image depicting a state of a region of interest of the subject irradiated with the illumination light is formed on the imaging surface of the imaging device 58 by the objective lens unit 56 and is captured through photoelectric conversion by the imaging device 58. An imaging signal (analog signal) of the captured endoscopic image of the subject is output from the imaging device 58.

The imaging signal (analog signal) of the endoscopic image output from the imaging device 58 is input to an A/D converter 64 through a scope cable 62. The A/D converter 64 converts the imaging signal (analog signal) from the imaging device 58 to an image signal (digital signal). The image signal obtained through the conversion is input to an image processing unit 70 of the processor device 16 through the connector section 32B.

The processor device 16 includes the control unit 68, the image processing unit 70, a storage unit 72, a distance detecting unit 78 (an example of distance detecting unit), and an image analyzing unit 80 (an example of image analyzing unit). The display device 18 and the input device 20 are connected to the control unit 68. The processor device 16 controls the light source control unit 22 of the light source device 12 and also performs image processing on an image signal of an endoscopic image received from the endoscope 14 and outputs the endoscopic image that has undergone the image processing to the display device 18 in response to an instruction input through an imaging switch of the endoscope 14 or the input device 20.

The processor device 16 may be constituted by using a computer, for example.

The image processing unit 70 performs various kinds of image processing, set in advance, on an image signal of an endoscopic image received from the endoscope 14 and outputs an image signal of the endoscopic image that has undergone the image processing. The image signal of the endoscopic image that has undergone the image processing is transmitted to the control unit 68.

In the case of performing size measurement of a lesion portion described below, the image signal of the endoscopic image that has undergone the image processing generated by the image processing unit 70 is also supplied to the distance detecting unit 78 and the image analyzing unit 80.

The endoscope 14 uses an ultra-wide-angle lens, and thus an endoscopic image is distorted due to the lens. Thus, it is preferable that the image processing unit 70 perform correction of distortion caused by the lens on the endoscopic image at least when size measurement of a lesion portion is performed. The correction of distortion caused by the lens may be performed by using a known method.

The distance detecting unit 78 measures the distance between the light emitting probe 60 and a subject when size measurement of a lesion portion described below is performed.

In the present invention, light having a regular pattern, such as a striped pattern, is emitted from the light emitting probe 60 onto a subject by using the light emitting probe 60 that emits light having a regular repetitive pattern so as to capture an image for measurement, which is an endoscopic image, for measuring the size of a lesion portion, the image for measurement is analyzed by the image analyzing unit 80, and thereby the size of a lesion portion is measured, which will be described in detail below.

If the light emitting probe 60 emits diffuse light as light having a regular pattern, the distance detecting unit 78 measures the distance between a subject and a tip portion of the light emitting probe 60 at the time of capturing of the image for measurement.

The image analyzing unit 80 analyzes the image for measurement and calculates at least one of the length and area of the lesion portion.

The distance detecting unit 78 and the image analyzing unit 80 will be described in detail below.

The control unit 68 controls the whole endoscopic diagnosis apparatus 10, specifically, display performed by the display device 18, the operation of the light source control unit 22, image processing performed by the image processing unit 70, and so forth. In addition, the control unit 68 controls the operation of the light source control unit 22 of the light source device 12 and performs control to, for example, store endoscopic images in units of images (in units of frames) in the storage unit 72 in response to an instruction from the imaging switch of the endoscope 14 or the input device 20.

The input device 20 is a known input device constituted by a keyboard, mouse, or the like. The display device 18 is a known display device (display) constituted by a liquid crystal display or the like.

As described above, the endoscopic diagnosis apparatus 10 according to the present invention has the light emitting probe 60 that emits light having a regular repetitive pattern.

The light emitting probe 60 is elongated and has a sufficient length so that it can be inserted from the forceps hole 30a of the endoscope 14 and extended through the forceps channel 50 and so that the tip portion thereof can be protruded from the forceps outlet 74 on the endoscope distal end surface 46, and the light emitting probe 60 emits light having a regular repetitive pattern, such as a striped pattern, from the tip portion.

The light emitting probe 60 may have various configurations using a light source, an elongated tubular body which has flexibility and through which a conductive line, optical fiber, or the like extends, a filter (mask) for emitting (projecting) light having a regular repetitive pattern, and so forth.

One exemplary configuration has an elongated tubular body having flexibility, a lens disposed at one end portion of the tubular body, a filter or the like for emitting light having a repetitive pattern, a light source disposed at the other end portion of the tubular body, an electrical system such as a switch for turning on/off the light source, and an optical fiber through which light emitted by the light source propagates to be applied onto the filter and which extends through the inside of the tubular body.

Alternatively, a light source, a filter for emitting light having a repetitive pattern, and an optical system such as a lens may be disposed at one end portion of an elongated tubular body having flexibility, and an electrical system such as a switch may be disposed at the end portion opposed to the optical system of the tubular body, with only a conductive line extending through the inside of the tubular body.

Hereinafter, the endoscopic diagnosis apparatus and lesion portion size measurement method according to the present invention will be described in detail by describing the operation of the endoscopic diagnosis apparatus 10.

A recording medium according to the present invention is a non-transitory computer-readable recording medium on which the program is recorded.

First, a description will be given of an operation in the case of capturing an endoscopic image.

At the time of normal capturing of an endoscopic image, the laser light source LD is lit up with a constant amount of light set in advance under control of the light source control unit 22. Laser light having a center wavelength of 445 nm and emitted by the laser light source LD is applied onto the fluorescent bodies 54A and 54B, and white light is emitted by the fluorescent bodies 54A and 54B. The white light emitted by the fluorescent bodies 54A and 54B is applied onto a subject, the reflected light thereof is received by the imaging device 58, and thereby an endoscopic image of the subject is captured.

An imaging signal (analog signal) of the endoscopic image output from the imaging device 58 is converted to an image signal (digital signal) by the A/D converter 64, various kinds of image processing are performed by the image processing unit 70, and the image signal of the endoscopic image that has undergone the image processing is output. Subsequently, the control unit 68 causes the display device 18 to display an endoscopic image corresponding to the image signal of the endoscopic image that has undergone the image processing, and if necessary, causes the storage unit 72 to store the image signal of the endoscopic image.

In the endoscopic diagnosis apparatus 10, size measurement of a lesion portion is performed in the following manner.

As described above, in the present invention, size measurement of a lesion portion is performed by using the light emitting probe 60 that emits light having a regular repetitive pattern.

Figure 5A:
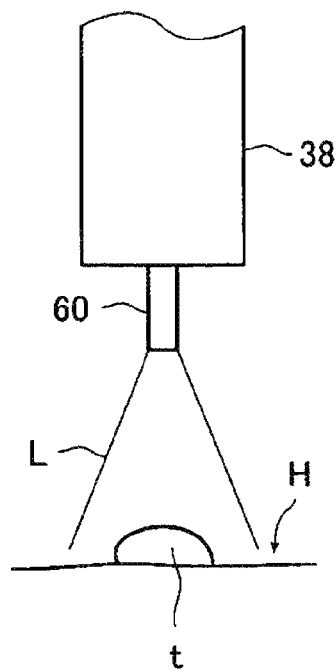
FIGS. 5A and 5B are conceptual diagrams for describing a lesion portion size measurement method according to the present invention.

In the case of performing size measurement of a lesion portion, an operator such as a surgeon inserts the light emitting probe 60 by inserting the tip portion on the light emission side of the light emitting probe 60 into the forceps hole 30a so as to cause the light emitting probe 60 to extend through the forceps channel 50 and the tip portion of the light emitting probe 60 to protrude from the endoscope distal end surface 46, as conceptually illustrated in FIG. 5A. Furthermore, the operator causes the light emitting probe 60 to emit light L having a regular repetitive pattern (hereinafter also referred to simply as pattern light L) onto a region of interest of a subject H.

During this time period, an endoscopic image of the subject H is captured and displayed on the display device 18, as described above.

At this time, if the operator provides an instruction to perform size measurement by using a switch or changing a mode, the endoscopic image captured by the endoscope 14 when the instruction to perform size measurement is provided is transmitted from the image processing unit 70 to the image analyzing unit 80 as an image for measurement that is used for performing size measurement of a lesion portion.

In this example, the pattern light L is light having a striped pattern in which linear (strip-shaped) light beams having a constant width are arranged at a constant interval in a direction orthogonal to a longitudinal direction, for example.

Figure 6A:
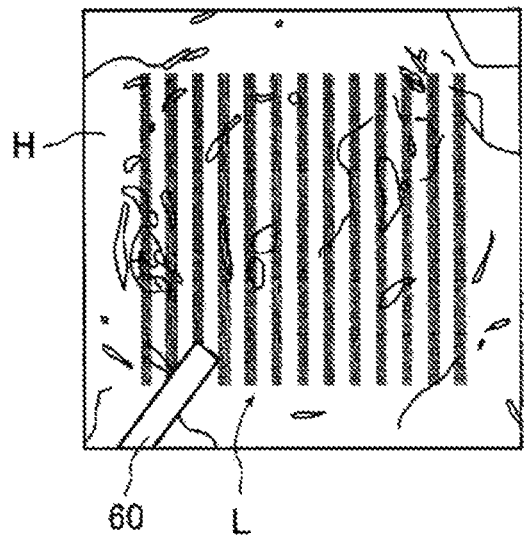
FIGS. 6A and 6B are conceptual diagrams for describing the lesion portion size measurement method according to the present invention.

As conceptually illustrated in FIG. 6A, if there is no lesion portion t such as a tumor portion in the subject H, the surface of the subject H is comparatively flat. Thus, the pattern light L on the subject H has a striped pattern that is almost the same as the pattern of the pattern light L emitted by the light emitting probe 60.

On the other hand, the lesion portion t such as a tumor portion has unevenness on its surface in both cases where the lesion portion t is of protruding type and flat type. Thus, if there is the lesion portion t such as a tumor portion in the region of interest of the subject H, the pattern light L on the subject H in the image for measurement (endoscopic image) has a pattern that is almost the same as the pattern of the pattern light L emitted by the light emitting probe 60 in a region with no lesion portion t, but in the lesion portion t, the pattern light L on the subject H is disturbed or distorted in accordance with the unevenness on the surface of the lesion portion t, as conceptually illustrated in FIG. 6B. That is, the pattern light L on the lesion portion t is different from the pattern light L emitted by the light emitting probe 60.

Thus, the lesion portion t can be detected by detecting a region in the image for measurement in which the pattern light L is different from the pattern light L emitted by the light emitting probe 60.

The shape (pattern) of the pattern light L emitted by the light emitting probe 60 being striped, and the width and interval of lines in the stripes are known. That is, the shape of the repetitive pattern of the pattern light L emitted by the light emitting probe 60 and the size of a unit of repetition in the repetitive pattern are known.

Thus, the size (length) S of the lesion portion t can be detected by analyzing the image for measurement, detecting a region in the image for measurement in which the pattern light L is different from the pattern light L emitted by the light emitting probe 60, and counting the number of lines in which the pattern light L is different.

If the pattern light L emitted by the light emitting probe 60 is parallel light, the width and interval of lines in the stripes of the pattern light L on the subject are identical to the width and interval of lines of the pattern light L emitted by the light emitting probe 60.

Thus, in this case, the image analyzing unit 80 analyzes the image for measurement supplied thereto, detects a region in the image for measurement in which the pattern light L is different from the pattern light L emitted by the light emitting probe 60, counts the number of lines in the region in which the pattern light L is different, and is thereby capable of calculating the size S of the lesion portion t on the basis of a count result and the width and interval of lines of the pattern light L emitted by the light emitting probe 60.

Alternatively, the image analyzing unit 80 may calculate the size S of the lesion portion t by counting the number of lines of the pattern light L that is different from the pattern light L emitted by the light emitting probe 60 in the image for measurement, without detecting a region.

As described above, if the pattern light L emitted by the light emitting probe 60 is parallel light, the distance detecting unit 78 does not need to perform any process. Alternatively, in the case of an endoscopic diagnosis apparatus compatible with only the light emitting probe 60 that emits pattern light L which is parallel light, it is not necessary to provide the distance detecting unit 78 in the processor device 16.

That is, if the pattern light L emitted by the light emitting probe 60 is parallel light, the size S of the lesion portion t can be measured through a simple process. However, the measureable size of the lesion portion t is limited in accordance with the size of the light emitting probe 60.

In contrast to this, if the pattern light L emitted by the light emitting probe 60 is diffuse light as illustrated in FIG. 5A, size measurement can be performed on lesion portions t having various sizes.

If the pattern light L emitted by the light emitting probe 60 is diffuse light, the size S of the lesion portion t is measured in the following manner.

If the pattern light L is diffuse light, an endoscopic image captured when an operator's instruction to perform size measurement is provided is supplied to the image analyzing unit 80 as an image for measurement in response to the instruction, as in the foregoing case. If the pattern light L is diffuse light, the image for measurement is also transmitted to the distance detecting unit 78.

Thereafter, the image (moving image) captured by the endoscope 14 and processed by the image processing unit 70 is continuously supplied to the distance detecting unit 78.

The operator may be allowed to input information indicating whether the pattern light L emitted by the light emitting probe 60 is diffuse light or parallel light by using a GUI (graphical user interface) or the like that uses the input device 20 and the display device 18.

However, such an operation is not necessary if the endoscopic diagnosis apparatus 10 is compatible with only the light emitting probe 60 that emits diffuse light or if the endoscopic diagnosis apparatus 10 is compatible with only the light emitting probe 60 that emits parallel light.

Figure 5B:
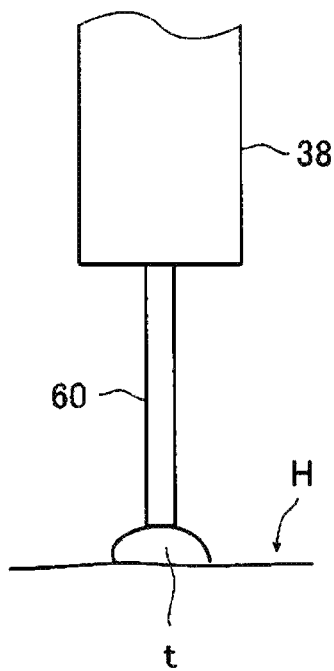

After providing the instruction to perform size measurement, the operator pushes the light emitting probe 60 (cause the light emitting probe 60 to extend) until the tip portion of the light emitting probe 60 comes in contact with the subject H, as conceptually illustrated in FIG. 5B.

After the image for measurement is supplied to the image analyzing unit 80 and the distance detecting unit 78 in response to the instruction to perform size measurement, display on the display device 18, output of a sound, or the like may prompt the operator to perform an operation of pushing the light emitting probe 60.

Upon the tip portion of the light emitting probe 60 corning in contact with the subject H as illustrated in FIG. 5B, the distance detecting unit 78 acquires the endoscopic image thereof.

In regard to detecting a state where the tip portion of the light emitting probe 60 is in contact with the subject H, a known method is available such as a method for detecting the state through an input operation using a GUI or the like perfoinied by an operator.

The following method is an exemplary preferable method for detecting a state where the tip portion of the light emitting probe 60 is in contact with the subject H.

As illustrated in FIG. 5A, the light emitting probe 60 emits the pattern light L from its tip portion. After an image for measurement is obtained, the endoscopic image captured by the endoscope 14 and processed by the image processing unit 70 is continuously supplied to the distance detecting unit 78.

The emission region of the pattern light L emitted by the light emitting probe 60 gradually becomes smaller as the light emitting probe 60 approaches the subject H. Thereafter, when the tip portion of the light emitting probe 60 comes in contact with the subject H, the pattern light L is blocked by the subject H and thus the amount of light received by the imaging device 58 rapidly decreases.

That is, the brightness of the endoscopic image captured by the endoscope 14 rapidly decreases when the tip portion of the light emitting probe 60 comes in contact with the subject H. In other words, the image data of the endoscopic image captured by the endoscope 14 rapidly fluctuates when the tip portion of the light emitting probe 60 comes in contact with the subject H.

Applying this theory, the distance detecting unit 78 analyzes the image data of an endoscopic image supplied thereto and detects the brightness of the endoscopic image after an image for measurement is supplied thereto, and when the brightness of the endoscopic image rapidly decreases, the distance detecting unit 78 determines that the tip portion of the light emitting probe 60 has come in contact with the subject H and acquires the endoscopic image in that state.

Subsequently, on the basis of the position of the tip portion of the light emitting probe 60 in the image for measurement and the position of the tip portion of the light emitting probe 60 in the endoscopic image in a state where the tip portion of the light emitting probe 60 is in contact with the subject H (hereinafter also referred to as an image for distance detection), the distance detecting unit 78 detects the distance between the tip portion of the light emitting probe 60 and the subject H (the region of interest of the subject H) at the time of capturing of the image for measurement.

As is known, a surgical instrument used with the endoscope 14 has a certain degree of rigidity though it has flexibility. Thus, the surgical instrument such as forceps that is inserted from the forceps hole 30a and protruded from the forceps outlet 74 is linearly protruded in a determined direction. That is, when the light emitting probe 60 is pushed until the tip portion thereof comes in contact with the subject H, the light emitting probe 60 moves linearly in a determined direction as shown in the image for measurement conceptually illustrated in FIG. 7A and the image for distance detection conceptually illustrated in FIG. 7B.

The surgical instrument protruded from the forceps outlet 74 is imaged in an endoscopic image. Here, the length of the surgical instrument imaged in the endoscopic image increases as the amount of protrusion of the surgical instrument from the forceps outlet 74 increases. Thus, as illustrated in FIGS. 7A and 7B, the length of the imaged light emitting probe 60 is larger in the image for distance detection than in the image for measurement.

In addition, the positional relationship between the forceps outlet 74 and the imaging device 58 is fixed.

Thus, the relationship between the length of protrusion of the surgical instrument from the forceps outlet 74 and the position of the tip portion of the surgical instrument in the endoscopic image is uniquely determined. In other words, the length of protrusion of the surgical instrument from the forceps outlet 74 can be uniquely detected on the basis of the position of the tip portion imaged in the endoscopic image.

Applying this theory, the distance between the tip portion of the light emitting probe 60 and the subject H at the time of capturing of the image for measurement can be detected by detecting, from the image for measurement illustrated in FIG. 7A, the length of protrusion of the light emitting probe 60 from the forceps outlet 74 at the time of capturing of the image for measurement, and further detecting, from the image for distance detection illustrated in FIG. 7B, the length of protrusion of the light emitting probe 60 from the forceps outlet 74 in a state where the tip portion of the light emitting probe 60 is in contact with the subject H, and by subsequently performing subtraction.

> Length of protrusion in contact state (image for distance detection)−Length of protrusion at the time of capturing of image for measurement=Distance between tip portion of probe and subject at the time of capturing of image for measurement That is, the optical path length of the pattern light L at the time of capturing of the image for measurement can be detected through the subtraction result.

The distance detecting unit 78 may detect the length of protrusion of the light emitting probe 60 from the forceps outlet 74 by using, for example, a LUT (look-up table), an arithmetic equation, or the like created in advance and representing the relationship between the position of the tip portion of the light emitting probe 60 in an endoscopic image captured by the endoscope 14 and the length of protrusion of the light emitting probe 60 from the forceps outlet 74.

The method for detecting the distance between the light emitting probe 60 (the tip portion of the light emitting probe 60) and the subject H at the time of capturing of the image for measurement is not limited to the above-described method.

That is, in the present invention, the distance between the light emitting probe 60 and the subject H at the time of capturing of the image for measurement can be detected by using various known methods for detecting the distance between a surgical instrument such as forceps and the subject H that are executed in an endoscopic diagnosis apparatus.

Alternatively, input unit for inputting the distance between the light emitting probe 60 and the subject H may be provided. An operator may measure the amount of movement of the light emitting probe 60 from the position at the time of capturing of the image for measurement to the position where the light emitting probe 60 comes in contact with the subject H and may input information of the amount of movement to the input unit, and the distance detecting unit 78 may detect the distance between the light emitting probe 60 and the subject H at the time of capturing of the image for measurement on the basis of the information of the amount of movement input to the input unit.

The distance detecting unit 78 supplies, to the image analyzing unit 80, the detection result of the distance between the tip portion of the light emitting probe 60 and the subject H at the time of capturing of the image for measurement.

The image analyzing unit 80 calculates the size S of the lesion portion t by using the image for measurement and the detection result of the distance supplied from the distance detecting unit 78.

The width and interval of lines in the pattern light L having a striped pattern emitted by the light emitting probe 60 are known. Also, the diffusion angle of the pattern light L from the light emitting probe 60 is known. Thus, the width and interval of lines in the pattern light L on the subject H, that is, the size of a unit of repetition in the repetitive pattern of the pattern light L, can be calculated by obtaining the distance between the light emitting probe 60 and the subject H at the time of capturing of the image for measurement.

After calculating the width and interval of lines in the pattern light L on the subject H in this manner, the image analyzing unit 80 analyzes the image for measurement as in the foregoing case where the pattern light L is parallel light so as to detect a region in the image for measurement in which the pattern light L is different from the pattern light L emitted by the light emitting probe 60, counts the number of lines in the region in which the pattern light L is different, and calculates the size S of the lesion portion t on the basis of the count result and the calculated width and interval of lines.

Alternatively, the image analyzing unit 80 may calculate the size S of the lesion portion t by counting the number of lines, in the pattern light L in the image for measurement, whose shapes are different from those in the pattern light L emitted by the light emitting probe 60, without detecting a region.

Figure 6B:
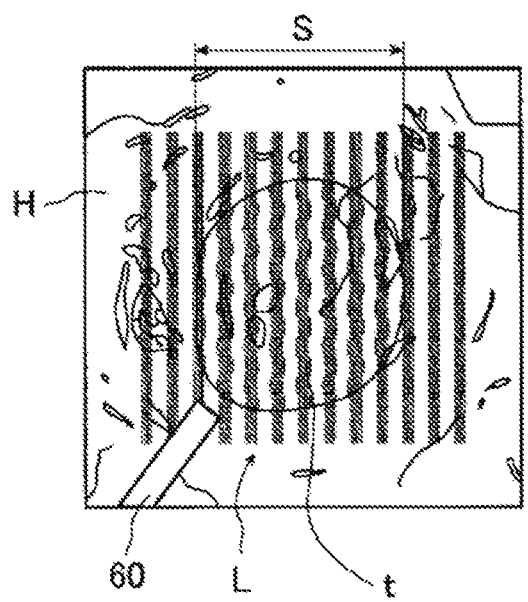

FIGS. 6A and 6B illustrate a state where the pattern light L having a striped pattern is emitted such that lines are arranged in the lateral direction in the figures.

However, in the present invention, the direction in which the lines are arranged is not essential, and the direction may be any of the lateral direction, vertical direction, and oblique direction. For example, if the lines are arranged in the vertical direction, the size S in a desired direction of the lesion portion t can be measured by changing the arrangement direction of the lines in the pattern light L on the subject H to the lateral or oblique direction by rotating the light emitting probe 60 around an axis which is the longitudinal direction thereof.

In the present invention, various sizes of the lesion portion t can be measured as well as the size of the lesion portion t in the arrangement direction of the lines in the pattern light L having a striped pattern.

For example, the number of pixels of the imaging device 58 corresponding to the size S in the image for measurement can be found out on the basis of the image for measurement. In addition, on the basis of the number of pixels corresponding to the size S in the image for measurement and the length corresponding to the size S obtained as a measurement result, the length on the subject H corresponding to the number of pixels in the image for measurement can be found out. Applying this theory, the number of pixels in a region in the image for measurement where the pattern light L is different from the pattern light L emitted by the probe in the longitudinal direction of lines in the pattern light L may be counted, and on the basis of the number of pixels and the length on the subject H corresponding to the number of pixels, the size of the lesion portion t in the longitudinal direction of the lines in the pattern light L may be measured.

Alternatively, over the whole region of the lesion portion t, the number of pixels in the arrangement direction and longitudinal direction of the lines in the pattern light L in the image for measurement may be counted, and the area of the lesion portion t may be measured by using the counted number of pixels and the length on the subject H corresponding to the number of pixels.

The size S of the lesion portion t measured by the image analyzing unit 80 is supplied to the control unit 68.

The control unit 68 displays the measurement result indicating the size S of the lesion portion t on the display device 18 and also, for example, stores (records) the measurement result in the storage unit 72. Preferably, the measurement result indicating the size S of the lesion portion t is stored in association with a corresponding endoscopic image, such as an endoscopic image captured when an instruction to perform size measurement is provided.

In addition, if the size S of the lesion portion t exceeds a threshold value set in advance, a warning may be output by displaying it on the display device 18 or outputting it as a sound.

In the above-described examples, the light emitting probe 60 emits light having a striped pattern as the pattern light L. In the present invention, the pattern light L may have any shape (pattern) as long as the pattern light L has a regular repetitive pattern.

For example, the light emitting probe 60 may emit, as the pattern light L, light having a lattice pattern in which lines are arranged in two directions orthogonal to each other. Accordingly, the size of the lesion portion t can be measured in the two directions orthogonal to each other by performing a process similar to that in the above-described example in the two arrangement directions of the lines.

A detailed description has been given of the endoscopic diagnosis apparatus, lesion portion size measurement method, and a non-transitory computer-readable recording medium according to the present invention. The present invention is not limited to the above-described examples, and various improvements and changes can of course be made without deviating from the gist of the present invention.

INDUSTRIAL APPLICABILITY

An embodiment of the present invention can be preferably applied to various diagnosis procedures using an endoscope.

REFERENCE SIGNS LIST

10 endoscopic diagnosis apparatus
12 light source device
14 endoscope
16 processor device
18 display device
20 input device
22 light source control unit
26 optical splitter
28 insertion section
30 operation section
30*a* forceps hole
32A, 32B connector section
34 flexible portion
36 bending portion
38 distal end portion
40 angle knob
42A, 42B illumination window
44 observation window
46 distal end surface
48A, 48B optical fiber
50 forceps channel
52A, 52B lens
54A, 54B fluorescent body
56 objective lens unit
58 imaging device
60 light emitting probe
62 scope cable
64 A/D converter
68 control unit
70 image processing unit
72 storage unit
74 forceps outlet
76 air/water supply channel opening
78 distance detecting unit
80 image analyzing unit
LD laser light source

What is claimed is:

1. An endoscopic diagnosis apparatus comprising:
an endoscope having a forceps outlet;
a light emitting probe for emitting diffuse light having a regular repetitive pattern, the light emitting probe being able to be protruded from the forceps outlet and be in contact with a subject; and
a processor configured to:
detect, from an image for measurement which is an image of the subject that is captured by the endoscope in a state where the diffuse light is emitted by the light emitting probe, a region in which a repetitive pattern is different from the repetitive pattern of the light emitted by the light emitting probe,
calculate at least one of a length and area of a lesion portion by using a number of repetitive patterns in the region in which the repetitive pattern is different and a size of a unit of repetition in the repetitive pattern, and
detect a distance between the light emitting probe and the subject at the time of capturing of the image for measurement, on the basis of a position of the light emitting probe in the image for measurement and a position of the light emitting probe in an image captured in a state where the light emitting probe is in contact with the subject, and
detect the size of the unit of repetition in the repetitive pattern on the subject by using the detected distance between the light emitting probe and the subject and a diffusion angle of the diffuse light.

2. The endoscopic diagnosis apparatus according to claim 1, wherein
the processor is configured to detect that the light emitting probe has come in contact with the subject, on the basis of a change in an amount of light emitted by the light emitting unit.

3. The endoscopic diagnosis apparatus according to claim 2, wherein
the regular repetitive pattern of the light emitted by the light emitting probe is a striped pattern or a lattice pattern.

4. The endoscopic diagnosis apparatus according to claim 1, wherein
the regular repetitive pattern of the light emitted by the light emitting probe is a striped pattern or a lattice pattern.

* * * * *